United States Patent [19]

Yokoyama et al.

[11] Patent Number: 4,605,786
[45] Date of Patent: Aug. 12, 1986

[54] PERFLUORO ETHER COMPOUND CONTAINING PERFLUOROCYCLOALKYL MOIETY

[75] Inventors: Kazumasa Yokoyama, Toyonaka; Yoshihisa Inoue, Kyoto; Taizo Ono, Tokyo; Chikara Fukaya, Osaka; Yoshio Arakawa, Suita; Youichiro Naito, Hirakata; Koichi Yamauchi, Sakai; Tadakazu Suyama, Kyoto, all of Japan

[73] Assignee: The Green Cross Corporation, Osaka, Japan

[21] Appl. No.: 563,436

[22] Filed: Dec. 20, 1983

[30] Foreign Application Priority Data

Dec. 21, 1982 [JP] Japan ................. 57-225226

[51] Int. Cl.$^4$ ............................. C07C 43/12
[52] U.S. Cl. ...................... 568/669; 514/832; 252/364
[58] Field of Search ........... 568/669, 683; 424/339; 514/832

[56] References Cited

U.S. PATENT DOCUMENTS

| | | | |
|---|---|---|---|
| 3,962,439 | 4/1976 | Yokoyama et al. | 424/248 |
| 4,024,192 | 5/1977 | Benninger et al. | 568/669 |
| 4,252,827 | 7/1981 | Yokoyama et al. | 424/366 |
| 4,423,061 | 3/1983 | Yokoyama et al. | 424/274 |
| 4,425,347 | 4/1984 | Yokoyama et al. | 424/256 |

OTHER PUBLICATIONS

Cady, Proceedings of the Chemical Society (London) Apr. 1960, pp. 133 & 136.
Riess et al. "Perfluoro Compounds as Blood Substitutes", Int'n. Ed. in English, Angewandte Chemie, vol. 17, No. 9, Sep. 1978, pp. 621–700.

Primary Examiner—Bernard Helfin
Attorney, Agent, or Firm—Cushman, Darby & Cushman

[57] ABSTRACT

A perfluoroether compound having the following formula is useful as a thermostable, inert solvent and inter alia as an oxygen carrier in an artificial blood or infusion fluid.

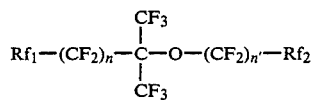

wherein $Rf_1$ and $Rf_2$ are different from each other and are selected from the group of a $C_1$ or $C_3$ perfluoroalkyl group which may be interrupted by an oxygen atom, and a $C_5$–$C_7$ perfluorocycloalkyl group, and n and n' are zero or an integer of 1; one of $Rf_1$ and $Rf_2$ being the $C_5$–$C_7$ perfluorocycloalkyl group and the total number of carbon atoms being 9–11 inclusive.

6 Claims, No Drawings

PERFLUORO ETHER COMPOUND CONTAINING PERFLUOROCYCLOALKYL MOIETY

This invention relates to a novel perfluoro ether compound, and more particularly to a perfluoro ether compound having a perfluorocycloalkyl moiety in the molecule, which is useful as a thermostable, inert solvent as well as an oxygen carrier in an artificial blood or in an infusion fluid.

The perfluoro ether compound of the present invention is represented by the formula $$Rf_1-(CF_2)_n-\underset{\underset{CF_3}{|}}{\overset{\overset{CF_3}{|}}{C}}-O-(CF_2)_{n'}-Rf_2 \quad (I)$$

wherein $Rf_1$ and $Rf_2$ are different from each other and are selected from the group of a $C_1$ to $C_3$ perfluoroalkyl group which may be interrupted by an oxygen atom, and a $C_5$-$C_7$ perfluorocycloalkyl group, and n and n' are zero or an integer of 1; one of $Rf_1$ and $Rf_2$ being the $C_5$-$C_7$ perfluorocycloalkyl group and the total number of carbon atoms being 9-11 inclusive.

The $C_5$-$C_7$ perfluoroalkyl group denoted by $Rf_1$ and $Rf_2$ is cyclopentyl, cyclohexyl or cycloheptyl group which is all perfluorinated. The perfluorocycloalkyl group is essentially present only one in the molecule and links to $$-\underset{\underset{CH_3}{|}}{\overset{\overset{CH_3}{|}}{C}}-$$

or to —O— optionally through —CF$_2$— in the molecule. When one of the $Rf_1$ and $Rf_2$ is the perfluorocycloalkyl group the other is $C_2$-$C_3$ perfluoroalkyl which may be interrupted by an oxygen atom.

The $C_1$ to $C_3$ perfluoroalkyl group containined in the present perfluoro ether compound is exemplified as perfluoro methyl, perfluoroethyl, perfluoro n-propyl and perfluoroisopropyl which may be interrupted by an oxygen atom so as to form perfluoro methoxymethyl, perfluoro methoxyethyl or perfluoro ethoxymethyl.

The perfluoro ether compound of the invention should have 9-11 carbon atoms in the molecule for giving good artificial blood in which the perfluoroether compound is emulsified in a physiologically acceptable aqueous medium.

The perfluoro ether compound (I) can be prepared, for example, by the fluorination, particularly the electrochemical fluorination, of a perhydrocompound corresponding to said compound (I) or of a partial hydro compound (I) or of a partial hydro compound corresponding to said compound (I). The partial hydro compound to be used preferably in a compound represented by the formula $$R-(CH_2)_n-\underset{\underset{CF_3}{|}}{\overset{\overset{CF_3}{|}}{C}}-O-(CH_2)_{n'}-R' \quad (II)$$

wherein R and R' denote a perhydro group corresponding to $Rf_1$ and $Rf_2$ of the formula (I), respectively; n and n' have the same meaning as above. When the method of electrochemical fluorination of the compound (II) is used, the perfluoro ether compound (I) can be obtained in a high yield even in the absence of an electric conductivity improver often needed for conventional electrochemical fluorination. Moreover, because of the presence of trifluoromethyl groups which are strong electron attractive groups in the compound (II), the ether linkage is trong and hardly broken, the amount of by-product formed by bond cleavage is small, and the perfluoro ether compound (I) is obtained with high purity.

The electrochemical fluorination of a perhydro compound or a partial hydro compound (II) corresponding to the above-mentioned perfluoro ether compound (I) is usually carried out in anhydrous hydrofluoric acid. Preferably, the starting compound is used in an amount corresponding to 0.1 to 0.3 mole for 1 liter of hydrofluoric acid. The electrolytic cell to be used may be those which are conventionally employed in the field of electrochemical fluorination. The electrochemical fluorination is normally performed at a current density of 0.2 to 3.0 A/dm$^2$ and a bath temperature of 3° to 10° C. and, in the case of batchwise operation, preferably carried out until the electrolytic voltage reaches at least 8 V. The addition of an electric conductivity improver (such as sodium fluoride) is optional.

The perfluoro ether compound (I) can be separated, when the starting compound (II) was fluorinated, as shown in the following example. Since most of the said compound (II) remains in the electrolytic cell and separates from hydrogen fluoride to form a lower layer, it is withdrawn from the cell after completion of the electrochemical fluorination. The mixture of the said compound (II) and the rearrangement product thereof is stirred under heating with an alkali-amine (sodium hydroxide-diisobutylamine etc.) mixture, washed, if necessary, with a potassium iodide-acetone mixture, and then separated by fractional distillation, preparative-scale gas chromatography etc.

The compound (II) is substantially known already, and is prepared by the reaction of a compound represented by the formula $$R-(CH_2)_n-\underset{\underset{CF_3}{|}}{\overset{\overset{CF_3}{|}}{C}}-OH \quad (III)$$

wherein R and n are the same as above, with a compound represented by the formula $$R'-(CH_2)_{n'}-X \quad (IV)$$

wherein X denotes a halogen atom such as chlorine or bromine; n' is the same as above, or by alkylating the former compound with an alkylsulfate such as dimethylsulfate or diethylsulfate.

The compound (III) may be obtained by using hexafluoroacetone according to the conventional method described, for example, by I. L. Knunyants et al. (Izv. Akad. Nauk SSSR Otd. Khim. Nauk, 1962, p. 684) or W. A. Sheppard [J. Am. Chem. Soc., 87, 2410 (1965)].

Since the perfluoro ether compound (I) of this invention not only can dissolve a large amount of oxygen and is chemically and biologically inert, but can be excreted rapidly from the body, it can form, for example, an aqueous emulsion containing 5 to 50, preferably 10 to 40, % (W/V) of the compound (I) to be used as an oxygen carrier in an artificial blood or in an infusion fluid for men and other mammals such as dogs, cats, cattle, mice, rats and guinea pigs.

The symbol "% (W/V)" referred to herein means the amount of the material by weight (gram) based on 100 ml of the resulting emulsion.

In the preparation of the emulsion mentioned above, there is used, as an emulsifier, a high molecular nonionic surfactant and/or phospholipids in an added amount of 1 to 5% (W/V).

As the medium for the emulsion, a physiologically acceptable aqueous solution is employed. If necessary, there may be added thereto such materials as glycerol to provide the desired isotonicity, and such plasma expanders as HES or dextran to regulate the colloid osmotic pressure of the emulsion.

The emulsion can be prepared by mixing the above-mentioned ingredients and homogenizing the mixture by means of, for example, a high-pressure jet type homogenizer until the particle diameters become 0.05 to 0.3 μm, preferably less than 0.2 μm.

EXAMPLE 1

Into an electrolytic cell made of Monel metal with an inner volume of 1.5 , which was provided with electrode plates (six plates as anode and seven plates as cathode) made of nickel (purity: 99.6% or higher) arranged alternately with an inter-electrode distance of 1.7–2.0 mm, the effective anode surface area being 10.5 dm$^2$, and with a reflux condenser made of copper at the upper part of the cell, was introduced 1.2 l of anhydrous hydrogen fluoride, and trace amounts of impurities were removed by preliminary electrolysis. Then, 0.16 mol of [1,1-bis(trifluoromethyl)butoxy]cyclopentane

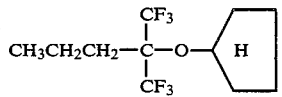

was introduced into the anhydrous hydrogen fluoride, and electrolysis was carried out, while introducing nitrogen gas from the bottom of the cell at a rate of 100 ml/min., under the conditions of anode current density of 0.3–1.0 A/dm$^2$, voltage 5.4–6.6 V and solution temperature of 3°–8° C. until the ampere-hours amounted to 154. No attempts was made to collect volatile products formed by a bond breaking reaction, which would give more yields of the whole products. After completion of the electrolysis, the contents of the cell separated into the upper layer of hydrogen fluoride and the lower layer of fluorocarbons. The lower layer was drained through the bottom of the cell, weighed 73.2 g (80.8% crude yield).

To the fluorocarbons thus separated, were added equal volumes of 70% aqueous potassium hydroxide solution and diisobutylamine, and the resulting mixture was refluxed for about three days. The reaction mixture was then mixed with an equal volume of water, cooled in an ice bath, and filtered by suction. The perfluoro compound sedimented as the lowermost layer were separated in a separatory funnel, washed successively with dilute sulfuric acid, concentrated sulfuric acid, saturated aqueous sodium hydrogen carbonate solution, water, 90% aqueous acetone solution containing 3% of potassium iodide, and water to yield 58 g of a transparent perfluoro compound.

The thus obtained perfluoro compound free from contaminants containing protons was subjected to simple distillation to give 47.1 g (52.0% yield) of a compound boiling at 145°–155° C.

The compound obtained above was subjected to preparative-scale gas chromatography to collect the desired product. This product was analyzed by spectroscopy (IR, 19F-NMR, MS), and was confirmed to be the objective compound, perfluoro[(1,1-dimethylbutoxy)cyclopentane]

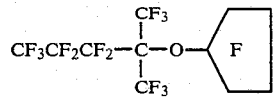

which is shown in Table 1 below as compound No. 12.

EXAMPLE 2

Under the same conditions as in Example 1, except for the addition of an electricity conductivity improver, 2-phenyl-2-methoxy-1,1,1,3,3,3-hexafluoropropane,

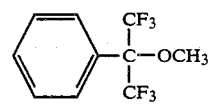

was fluorinated. Almost no polymerization, which is characteristic of electrochemical fluorination of compounds having an aromatic nucleus, was observed. The reaction product was, after alkali-amine treatment and potassium iodide-acetone treatment, subjected to simple distillation to give a product in a 53.2% yield. The isolated compound by using preparative-scale gas chromatography was analyzed by spectroscopy (IR, 19F-NMR, MS), and was confirmed to be the objective compound, perfluoro[(1-methoxy-1-methylethyl)cyclphexane]of the formula,

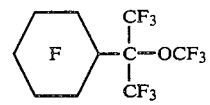

which is shown as Compound No. 1 in Table 1 below.

A series of other perfluoro ether compounds was synthesized in exactly the same manner or in the same manner except the addition of sodium fluoride as that described above. Each product was, after purification and fractional distillation, isolated by using preparative-scale gas chromatography and confirmed to be the objective compound (I) upon analysis by spectroscopy (IR, 19F-NMR, MS). The name, the structural formula, and the boiling point of each of the objective compounds (I) were as shown in the following Table 1.

Each of the structural formula shown in Table 1 implies that all the carbon atoms are saturated with fluorine atoms, and the fluorocarbon groups therein are abbreviated.

For example, the formula

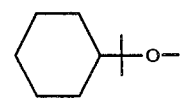

indicates in its exact meaning the formula

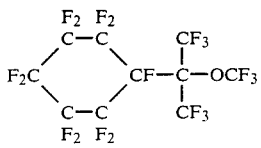

of the product of Example 2.

TABLE 1

| Compound No. | Name | Structural formula | Boiling pt. (°C.) |
|---|---|---|---|
| 1 | Perfluoro[(1-methoxy-1-methylethyl)cyclohexane] | | 130–140 |
| 2 | Perfluoro[(1-ethoxy-1-methylethyl)cyclohexane] | | 144–154 |
| 3 | Perfluoro{[1-methoxy-methoxy)-1-methylethyl]-cyclohexane] | | 146–157 |
| 4 | Perfluoro[(1-methoxy-1-methylethyl)-cycloheptane] | | 144–154 |
| 5 | Perfluoro[2-methoxy-2-methylpropyl)-cyclopentane] | | 145–155 |
| 6 | Perfluoro[(1-ethoxy-1-methylethyl)cycloheptane] | | 130–139 |
| 7 | Perfluoro{[1-methoxy-methoxy)-1-methylethyl]-cyclopentane] | | 130–139 |
| 8 | Perfluoro[(1-methoxy-1-methylethyl)cyclopentane] | | 114–122 |
| 9 | Perfluoro[1-methyl-1-propoxyethyl)cyclopentane] | | 145–156 |
| 10 | Perfluoro[(1-methyl-1-isopropoxyethyl)-cyclopentane] | | 144–154 |
| 11 | Perfluoro{[1-(ethoxy-methoxy)-1-methyl-ethyl]cyclopentane] | | 147–158 |
| 12 | Perfluoro[(1,1-dimethylbutoxy)cyclopentane] | | 145–155 |
| 13 | Perfluoro[(1,1,2-trimethylpropoxy)cyclopentane] | | 145–155 |
| 14 | Perfluoro[(2-ethoxy-1,1-dimethylethoxy)-cyclopentane] | | 149–159 |
| 15 | Perfluoro[(1,1-dimethylpropoxy)cyclopentane] | | 130–140 |
| 16 | Perfluoro[2-methoxy-1,1-dimethylethoxy)-cyclopentane] | | 132–142 |
| 17 | Perfluoro[(1,1-dimethylpropoxy)cyclohexane | | 146–155 |
| 18 | Perfluoro[(2-methoxy-1,1-dimethylethoxy)-cyclohexane | | 148–157 |
| 19 | Perfluoro(tert-butoxy-cyclohexane) | | 129–139 |
| 20 | Perfluoro(tert-butoxycyclopentane) | | 114–124 |
| 21 | Perfluoro(tert-butoxycyclopentane) | | 146–155 |
| 22 | Perfluoro[tert-butoxy-methyl)cyclohexane | | 147–156 |

What is claimed is:

1. A perfluoro ether compound represented by the formula

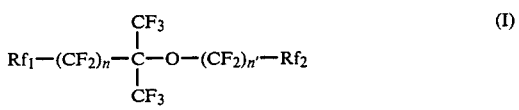

wherein $Rf_1$ and $Rf_2$ are different from each other and are selected from a $C_1$ to $C_3$ perfluoroalkyl group, which may be interrupted by an oxygen atom, and a $C_5$–$C_7$ perfluorocycloalkyl group, and n and n' are zero or an integer of 1; provided that one of $Rf_1$ and $Rf_2$ is $C_5$–$C_7$ perfluorocycloalkyl group and the the total number of carbon atoms is 9–11 inclusive.

2. The perfluoro ether compound of claim 1, having the formula (I), in which $Rf_1$ is a perfluoro $C_5$–$C_7$ cycloalkyl group, and $Rf_2$ is a $C_1$ to $C_3$ perfluoroalkyl group which may be interrupted by an oxygen atom.

3. The perfluoro ether compound of claim 1, having the formula (I), in which $Rf_1$ is a $C_1$ or $C_3$ perfluoroalkyl group which may be interrupted by an oxygen atom, and $Rf_2$ is a perfluoro $C_5$–$C_7$ cycloalkyl group.

4. The perfluoroether compound of claim 1, in which the perfluoro $C_5$–$C_7$ cycloalkyl group is selected from the group consisting of perfluorocyclopentyl, perfluorocyclohexyl and perfluoroheptyl groups.

5. The perfluoro ether compound of claim 1, in which the $C_1$ to $C_3$ perfluoroalkyl group is selected from the group consisting of perfluoro methyl, perfluoro ethyl, perfluoro n-propyl and perfluoro isopropyl groups.

6. The perfluoro ether compound of claim 1, in which the oxygen atom-interrupted $C_1$ to $C_3$ perfluoroalkyl group is selected from the group consisting of perfluoro methoxy, perfluoro methoxymethyl, perfluoro methoxyethyl and perfluoroethoxymethyl groups.

* * * * *